(12) United States Patent
Kanda et al.

(10) Patent No.: US 6,730,106 B2
(45) Date of Patent: May 4, 2004

(54) VITREOUS SURGICAL APPARATUS

(75) Inventors: Hidenori Kanda, Okazaki (JP); Hideo Oda, Gamagori (JP); Hiroyuki Tashiro, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 143 days.

(21) Appl. No.: 09/977,342

(22) Filed: Oct. 16, 2001

(65) Prior Publication Data

US 2002/0049461 A1 Apr. 25, 2002

(30) Foreign Application Priority Data

Oct. 20, 2000 (JP) ........................................ 2000-326986

(51) Int. Cl.[7] .............................................. A61B 17/32
(52) U.S. Cl. .......................................... 606/171; 604/22
(58) Field of Search ................................. 606/169, 170, 606/171, 172, 173, 167, 168; 604/22

(56) References Cited

U.S. PATENT DOCUMENTS

| 4,650,460 A | * | 3/1987 | Roizenblatt | 604/22 |
| 4,940,468 A | * | 7/1990 | Petillo | 606/170 |
| 5,047,008 A | * | 9/1991 | de Juan et al. | 604/22 |
| 5,226,910 A | * | 7/1993 | Kajiyama et al. | 606/171 |
| 5,487,725 A | * | 1/1996 | Peyman | 604/22 |
| 5,562,691 A | * | 10/1996 | Tano et al. | 606/166 |
| 5,810,765 A | * | 9/1998 | Oda | 604/31 |
| 5,979,494 A |   | 11/1999 | Perkins et al. | |
| 6,258,111 B1 | * | 7/2001 | Ross et al. | 606/171 |
| 6,383,203 B1 | * | 5/2002 | Makihara | 606/171 |
| 6,527,745 B1 | * | 3/2003 | Kanda et al. | 604/151 |

FOREIGN PATENT DOCUMENTS

| JP | A 2001-87303 | 4/2001 |
| WO | WO 97/46164 A1 | 12/1997 |
| WO | WO 01/15640 A1 | 3/2001 |
| WO | WO 01/30281 A1 | 5/2001 |

OTHER PUBLICATIONS

U.S. patent application Ser. No. 09/669,727.

* cited by examiner

Primary Examiner—Julian W. Woo
Assistant Examiner—Victor X Nguyen
(74) Attorney, Agent, or Firm—Oliff & Berridge, PLC

(57) ABSTRACT

A vitreous surgical apparatus in which an inner tubular blade is moved in an axis direction with respect to an outer tubular blade by supply and exhaust of compressed air to excise a part of a vitreous body in an eyeball and aspirate and discharge the excised part out of the eyeball, the apparatus including: a plurality of solenoid valves each of which is opened and closed for performing the supply and exhaust of the compressed air; and a control unit which synchronously drives the solenoid valves to open and close in order to move the inner tubular blade at a desired cutting speed.

12 Claims, 4 Drawing Sheets

FIG.5

| CUTTING SPEED CV (cpm) | CYCLE TIME ST (msec) | CLOSE TIME T1 (msec) | OPEN TIME T2 (msec) | OPEN RATIO T2/ST (%) |
|---|---|---|---|---|
| 50 | 1200.0 | 50 | 1150.0 | 96 |
| 100 | 600.0 | 50 | 550.0 | 92 |
| 150 | 400.0 | 50 | 350.0 | 88 |
| 200 | 300.0 | 50 | 250.0 | 83 |
| 250 | 240.0 | 50 | 190.0 | 79 |
| 300 | 200.0 | 50 | 150.0 | 75 |
| 350 | 171.4 | 50 | 121.4 | 71 |
| 400 | 150.0 | 50 | 100.0 | 67 |
| 450 | 133.3 | 50 | 83.3 | 63 |
| 500 | 120.0 | 48 | 72.0 | 60 |
| 550 | 109.1 | 44 | 65.1 | 60 |
| 600 | 100.0 | 40 | 60.0 | 60 |
| 650 | 92.3 | 37 | 55.3 | 60 |
| 700 | 85.7 | 34 | 51.7 | 60 |
| 750 | 80.0 | 32 | 48.0 | 60 |
| 800 | 75.0 | 30 | 45.0 | 60 |
| 850 | 70.6 | 28 | 42.6 | 60 |
| 900 | 66.7 | 26 | 40.7 | 61 |
| 950 | 63.2 | 24 | 39.2 | 62 |
| 1000 | 60.0 | 22 | 38.0 | 63 |
| 1050 | 57.1 | 21 | 36.1 | 63 |
| 1100 | 54.5 | 20 | 34.5 | 63 |
| 1150 | 52.2 | 19 | 33.2 | 64 |
| 1200 | 50.0 | 18 | 32.0 | 64 |
| 1250 | 48.0 | 17 | 31.0 | 65 |
| 1300 | 46.2 | 16 | 30.2 | 65 |
| 1350 | 44.4 | 15 | 29.4 | 66 |
| 1400 | 42.9 | 14 | 28.9 | 67 |
| 1450 | 41.4 | 13 | 28.4 | 69 |
| 1500 | 40.0 | 12 | 28.0 | 70 |
| 1550 | 38.7 | 11.5 | 27.2 | 70 |
| 1600 | 37.5 | 11 | 26.5 | 71 |
| 1650 | 36.4 | 11 | 25.4 | 70 |
| 1700 | 35.3 | 10.5 | 24.8 | 70 |
| 1750 | 34.3 | 10 | 24.3 | 71 |
| 1800 | 33.3 | 10 | 23.3 | 70 |

VITREOUS SURGICAL APPARATUS

BACKGROUND OF THE INVENTION

1. Field of the Invention

The present invention relates to a vitreous surgical apparatus for excising a part of a vitreous body in an eyeball, and aspirating and discharging the excised part out of the eyeball.

2. Description of Related Art

A vitreous body cutter used in vitreous surgery is operated to excise a part of a vitreous body in an eyeball of a patient's eye by moving an inner tubular blade in an outer tubular fixed blade while drawing the part of the vitreous body by aspiration into an aspiration port provided in one end of the outer blade.

As such moving system of the inner blade, there has been known a guillotine type which moves an inner blade to reciprocate.

Moreover, as systems for driving an inner blade, there are an electrical system using a vitreous body cutter which mounts therein an electric motor or electromagnet, and a pneumatic system which drives an inner blade by repeating supply and exhaust of compressed air. This pneumatic system intermittently performs supply of compressed air from a compression pump into a cylinder constituted of a piston, a diaphragm, and others and exhaust of the air from the cylinder by control of opening and closing of a solenoid valve.

In vitreous surgeries, in particular, operations on the periphery of a retina, speedup of a cutting speed (a cutting rate) of the vitreous body cutter is requested. Accordingly, the number of reciprocating motions of the inner blade per unit of time needs to be increased.

To realize high-speed actuation of the pneumatically operated cutter, the solenoid valve which controls the supply of compressed air to the cutter needs a high responsivity for the supply of compressed air. Thus, the solenoid valve has to be designed to have an air flow passage of a larger effective diameter (caliber) and to open and close at a high speed. There is, however, no solenoid valve satisfying those requirements at present. Newly designing a solenoid valve with an air flow passage of a larger effective diameter will result in high cost. Hence it is difficult to materialize a high-speed cutter for vitreous surgery. Furthermore, a large-sized solenoid valve is usually slow in response speed. It is therefore difficult to produce a solenoid valve with high responsivity and capable of allowing a large amount of flow. Also, the large solenoid valve generally has a high noise problem.

If the vitreous body cutter is driven at a high speed, an open time of the aspiration port in the end of the cutter (outer blade) in each cycle is reduced than when actuated at a low speed. This would cause problems that aspiration efficiency lowers and cutting sharpness of the cutter with respect to a vitreous body deteriorates.

SUMMARY OF THE INVENTION

The present invention has been made in view of the above circumstances and has an object to overcome the above problems and to provide a vitreous surgical apparatus capable of actuating a cutter for vitreous surgery at a high speed by a simple structure, and enhancing cutting sharpness of the cutter actuated at a high speed.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a vitreous surgical apparatus in which an inner tubular blade is moved in an axis direction with respect to an outer tubular blade by supply and exhaust of compressed air to excise a part of a vitreous body in an eyeball and aspirate and discharge the excised part out of the eyeball, the apparatus including: a plurality of solenoid valves each of which is opened and closed for performing the supply and exhaust of the compressed air; and control means which synchronously drives the solenoid valves to open and close in order to move the inner tubular blade at a desired cutting speed.

According to another aspect of the present invention, there is provided a vitreous surgical apparatus for excising a part of a vitreous body in an eyeball and aspirating and discharging the excised part out of the eyeball, the apparatus including: an outer tubular blade; an inner tubular blade movable in an axis direction with respect to the outer tubular blade; a piston to which the inner tubular blade is fixed; an air chamber in which the piston is movably disposed; a plurality of solenoid valves each having an output port being in communication with the air chamber, an aspiration port being in communication with a compressed air supply source, and an exhaust port through which the compressed air is exhausted, the solenoid valve being switched between communication between the output port and the aspiration port and communication between the output port and the exhaust port to alternately perform supply and exhaust of compressed air to and from the air chamber; and a control section which controls switching in each of the solenoid valves to move the inner tubular blade at a desired cutting speed.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 5 is an explanatory view showing examples of OPEN and CLOSE times of an aspiration port of the cutter and a ratio of the OPEN time to one cycle time with reference to a set value of a cutting speed.

DETAILED DESCRIPTION OF THE PREFERRED EMBODIMENTS

Figure 1:
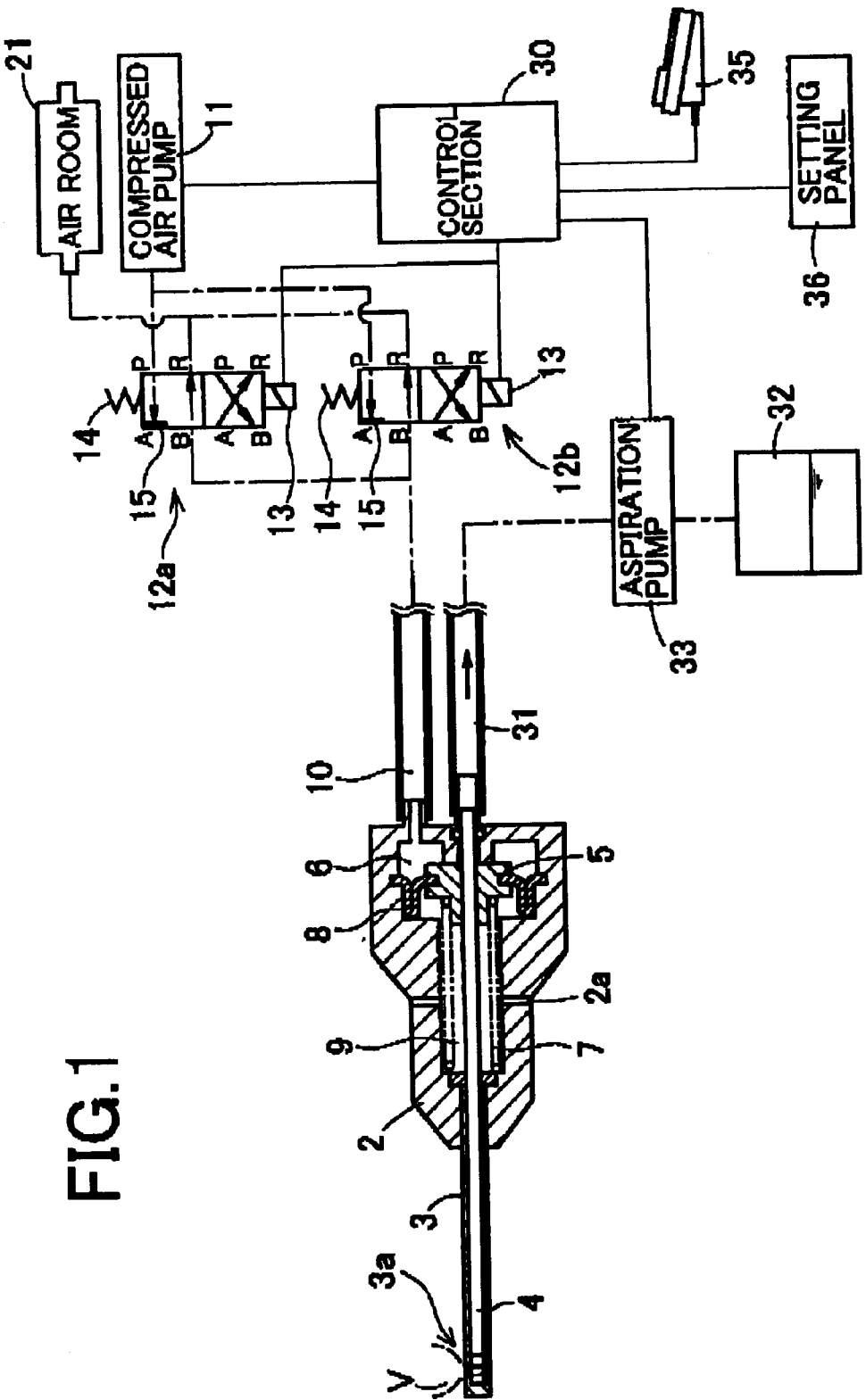
FIG. 1 is a schematic structural view of a vitreous surgical apparatus in an embodiment according to the present invention.

A detailed description of a preferred embodiment of a vitreous surgical apparatus embodying the present invention will now be given referring to the accompanying drawings. FIG. 1 is a schematic structural view of a vitreous surgical apparatus in the present embodiment.

A cutter 1 for vitreous surgery (hereinafter, referred to as a vitreous body cutter), which is a handpiece, is constructed such that an outer tubular blade 3 with an aspiration port 3a in an end portion is partially and fixedly disposed in a housing 2, an inner tubular blade 4 is fit in the outer blade 3 to be slidably in an axis direction, and a piston 5 is fixed on the inner blade 4. This inner blade 4 is of a hollow-body shape and a cutting edge at one end. The piston 5 is movably connected in the housing 2 through a diaphragm 8. Thus, the housing 2, the piston 5, and the diaphragm 8 define a compartment 9 and an air chamber 6.

In the compartment 9, a spring 7 is disposed urging the piston 5 toward the air chamber 6. A moving force is thus applied to the piston 5 in a return (backward) direction, i.e., rightward in FIG. 1. The housing 2 is provided with a hole 2a having one end which communicates with the compartment 9. This hole 2a allows an air flow in/from the compartment 9, so that the pressure in the compartment 9 can be maintained at atmospheric pressure even when movement of the piston S causes a change in volume of the compartment 9, thus preventing unnecessary force from being applied to the piston 5.

Figure 2:
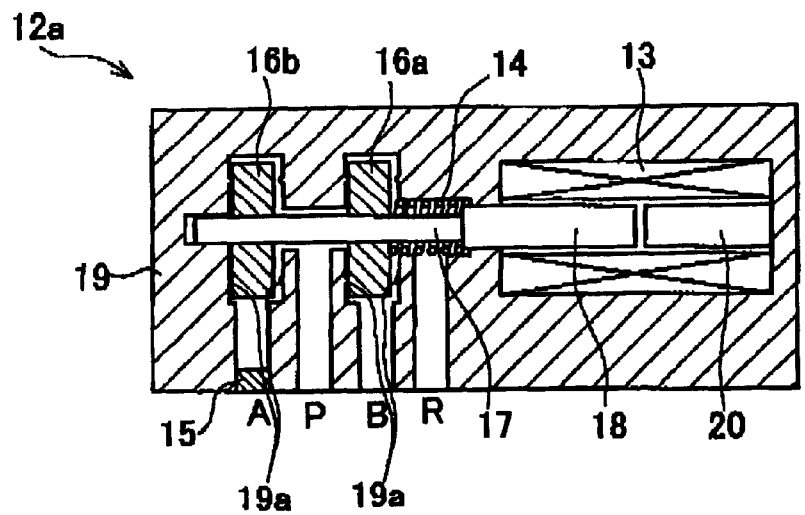
FIG. 2 is a schematic structural view of a solenoid valve of the apparatus in the embodiment.

The air chamber 6 in the cutter 1 is connected to two solenoid valves 12a and 12b which intermittently supply compressed air to the chamber 6 through a tube 10. FIG. 2 is a schematic structural view of one of the solenoid valves. Since both the solenoid valves 12a and 12b are of the same structure, only the solenoid valve 12a is explained below.

The solenoid valve 12a has a housing 19 in which two valves 16a and 16b are fixed on a shaft 17 having an end fixedly connected to a movable core 18. A fixed core 20 is arranged adjacently to the movable core 18 and one end of the core 20 is fixed to the housing 19. The two valves 16a and 16b are both urged by a force of a spring 14 in the direction opposite to an electromagnetic coil 13. The housing 19 is provided with an aspiration port P, an exhaust port R, an output port A, and an output port B.

These ports are in communication with each other in the housing 19 as shown in FIG. 2. Projections 19a are each formed in a circle in the housing 19 in which the valves 16a and 16b are moved. These projections 19a serve as a seal which comes into contact with the valves 16a and 16b. Upon application of electric current to the electromagnetic coil 13, the movable core 18 is attracted toward the fixed core 20 on the principle of electromagnet, moving the shaft 17 and the valves 16a and 16b rightward in the figure. When the valves 16a and 16b are moved rightward, the aspiration port P is brought into communication with the output port B (the solenoid valve 12a is opened). Upon stop of the application of electric current to the electromagnetic coil 13, to the contrary, the valves 16a and 16b are moved leftward in the figure by the urging force of the spring 14, providing communication between the exhaust port R and the output port B and between the aspiration port P and with the output port A (the solenoid valve 12a is closed). It is to be noted that the output port A is blocked with a blind stopper 15. When the application of electric current to the coil 13 is stopped, therefore, the aspiration port P is put in a blocked state.

The tube 10 connected to the air chamber 6 in the cutter 1 bifurcates into two passages connected to the output ports B of the solenoid valves 12a and 12b respectively. The aspiration ports P of the solenoid valves 12a and 12b are connected to an air supply port of the compressed air pump 11. The exhaust ports R of the solenoid valves 12a and 12b are connected to an air room 21 for reduction of exhaust noise. Conventionally, a muffler of a sponge type is attached to the exhaust port of a solenoid valve. This sponge type muffler provides only a small muffling effect and therefore high noise is produced when plural solenoid valves are provided. To enhance the muffling effect, in the present embodiment, the air room 21 of a cylinder type is attached as a muffler.

By opening and closing of the solenoid valves 12a and 12b, compressed air is supplied (pumped) from the compressed air pump 11 in the air chamber 6 in the cutter 1 and exhausted from the air chamber 6. Thus, the inner tubular blade 4 fixed to the piston 5 is reciprocated in the outer tubular blade 3, thereby excising a part of a vitreous body V drawn by aspiration into the aspiration port 3a.

An aspiration passage of the inner blade 4 is joined to an end of an aspiration tube 31. The other end of the aspiration tube 31 is connected to a waste liquid bag 32. When an aspiration pressure is applied into the inner blade 4 by an aspiration pump 33, the excised part of the vitreous body V is aspirated from the aspiration port 3a and discharged into the bag 32 through the inner blade 4 and the tube 31.

In FIG. 1, numeral 30 is a control section of the surgical apparatus in the present embodiment. This control section 30 controls and drives the solenoid valves 12a and 12b, the compressed air pump 11, the aspiration pump 33, and others, in accordance with operation signals from a foot switch 35 and setting signals from a setting panel 36.

Operation of the vitreous surgical apparatus structured as above is explained below.

Figure 3:
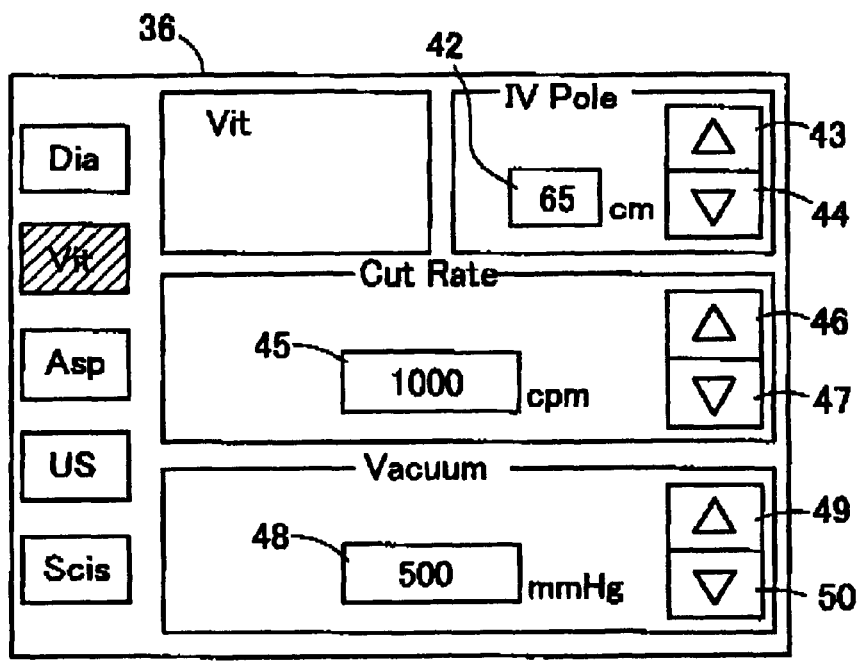
FIG. 3 is a view of a setting panel screen for a vitreous surgical mode.

For preparation of surgery, an operator (surgeon) sets various conditions for vitreous surgical operation with switches on the setting panel 36 of a touch panel type shown in FIG. 3. To set an irrigation pressure, a set value 42 of a height of an irrigation pole is adjusted with an UP button 43 and a DOWN button 44. Similarly, a set value 45 of a cutting speed (cutting rate) of the cutter 1 is adjusted with an UP button 46 and a DOWN button 47, and a set value 48 of an aspiration pressure of the aspiration pump 33 is adjusted with a UP button 49 and a DOWN button 50.

The operator injects irrigation fluid from an irrigation bottle into the eye of a patient and also inserts the outer blade 3 of the cutter 1 into the eye so that the aspiration port 3a is positioned in an affected part such as opacity. Then, the operator presses the footswitch 35 to drive the compressed air pump 11 and the aspiration pump 33, thereby operating the cutter 1 at the cutting speed and aspiration pressure previously set as above.

The control section 30 controls and drives the solenoid valves 12a and 12b at the set cutting speed. When electric current is applied to the solenoid valves 12a and 12b (more specifically, to respective electromagnetic coils 13) in response to a control signal from the control section 30, the aspiration port P is brought into communication with the output port B in each of the solenoid valves 12a and 12b, thereby allowing the compressed air to flow from the compressed air pump 11 to the air chamber 6 through the tube 10. This moves the piston 5 in a forward direction, thus moving the inner blade 4 fixed to the piston 5 along the outer blade 3, cutting the part of the vitreous body V being drawn into the aspiration port 3a. When the application of electric current to the solenoid valves 12a and 12b is stopped, the exhaust port R is brought into communication with the output port B in each of the solenoid valves 12a and 12b, thereby allowing the compressed air to flow from the air chamber 6 to the air room 21 serving for noise reduction, and the air is then released into the atmosphere. Accordingly, the piston 5 is moved in a backward direction (rightward in FIG.

1) by the urging force of the spring 7. With the backward motion of the piston 5, the inner blade 4 is slid in the outer blade 3 in a return direction. This allows the aspiration port 3a to open, aspirating the vitreous body V into the aspiration port 3a.

Figure 4:
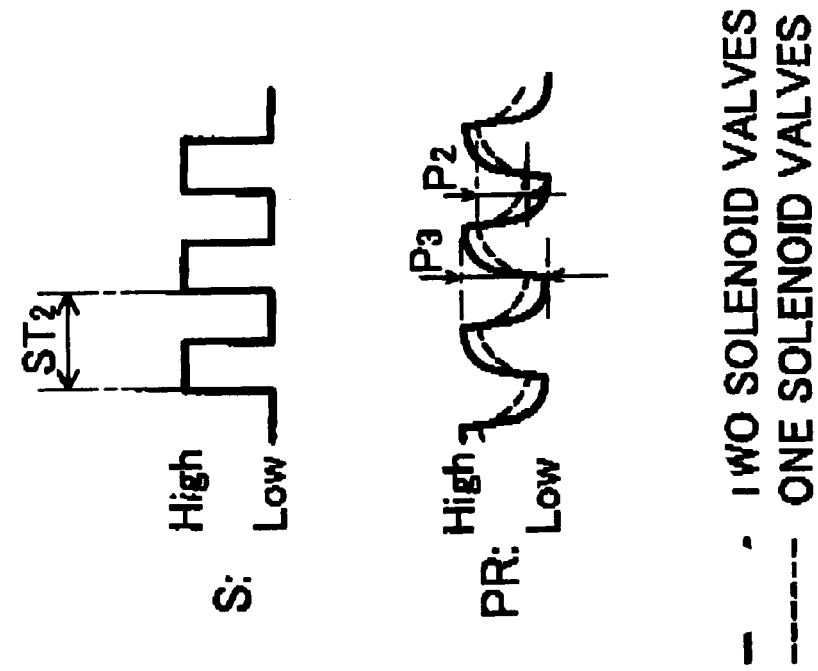
FIG. 4A and FIG. 4B are graphs each showing a relationship between a driving speed of the solenoid valve and a driving pressure to the vitreous body cutter.
Figure 4:
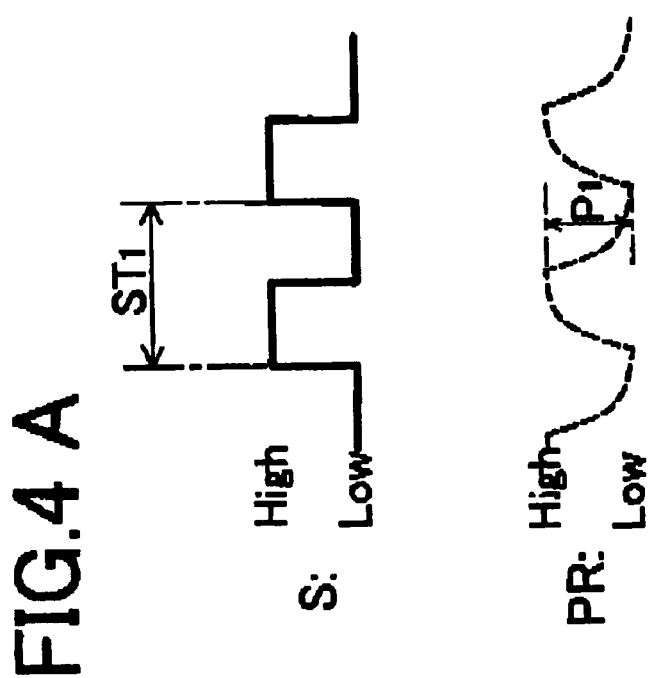

Now, differences between the case where a single solenoid valve is used and the case where two solenoid valves are used as in the present embodiment are explained below with reference to FIG. 4. FIG. 4A is a graph showing a relationship between the driving speed of the solenoid valve and the driving pressure of the cutter 1 (i.e., the pressure of the compressed air to be supplied to the air chamber 6) in the case where the cutting speed of the cutter 1 is adjusted to a low setting (a cycle time $ST_1$). FIG. 4B is a graph showing a relationship between those in the case where the cutting speed is adjusted to a high setting (a cycle time $ST_2$).

When a driving signal S turns High, the solenoid valve 12a is energized, allowing the compressed air to flow from the compressed air pump 11 to the air chamber 6. The driving pressure PR increases accordingly. When the driving signal S turns Low, to the contrary, the application of electric current is stopped, allowing the air chamber 6 to open to the atmosphere. The driving pressure PR then decreases. A conventional cutting speed is in a range from about 600 to 800 cpm. At such a cutting speed, as shown in FIG. 4A, even only a single solenoid valve could control the driving pressure PR in the range of variation $P_1$ sufficient to actuate the inner blade 4 in an enough stroke (travel).

If the cutting speed is requested to increase up to about 1200 to 1800 cpm, a solenoid valve capable of operating at a high speed is used. As the opening and closing rate of the valve 12a is increased, the cutting speed itself can be raised.

However, a typical solenoid valve capable of operating at a high speed has a small effective diameter of an air flow passage, which can neither feed the sufficient amount of compressed air to the cutter 1 in a short time nor exhaust the compressed air in a short time. As a result thereof, as indicated by a dotted line in FIG. 4B, the driving pressure PR descends before full ascent due to the stop of supply of the compressed air, while ascends before full descent due to the start of supply of the compressed air. In other words, the pressure PR is changed only by the range of variation $P_2$ in the figure. The inner blade 4 therefore could not be moved to reciprocate in an enough stroke. This prevents full open and close of the aspiration port 3a of the outer blade 3, which deteriorates excision and aspiration (cutting sharpness) with respect to the vitreous body V.

On the other hand, the use of a plurality of the solenoid valves 12a and 12b makes it possible to carry out high-speed opening and closing operations and also increase the air flow passage. This enables quick start of supply of the compressed air to the cutter 1 and sufficient release of the air. The driving pressure PR is, as indicated by a solid line in FIG. 4B, controlled to change in the variation range $P_3$ (almost the same as $P_1$) enough for operating the inner blade 4 in a sufficient stroke, as in the case of the low-speed operation. Consequently, the excision and aspiration with respect to the vitreous body V can be ensured.

When two or more solenoid valves are used, even if one of those valves breaks down due to for example clogging, other valves are still workable. Even in case the trouble may arise, therefore, the surgery can be continuously performed at a low cutting speed (600–800 cpm).

As above, the cutter 1 can be driven at a high speed, enabling intermittent short-time aspiration in the surgery on the periphery of a retina. This makes it possible to reduce the behavior of the retina to smoothly excise the vitreous body without aspirating the retina. In the surgery on the center portion of the eyeball, on the other hand, the cutter 1 is used at the cutting speed in a range of 600–800 cpm which provides a good aspiration efficiency. The cutting speed set value 45 is changed by operation of the UP button 46 and the DOWN button 47.

When the cutting speed set value 45 is changed, the control section 30 changes times for opening and closing the solenoid valves 12a and 12b and the ratio of a closing time thereof to a cycle time in accordance with the set value, as shown in FIG. 5. In FIG. 5, a CLOSE time T1 indicates a time interval to close the aspiration port 3a formed in the end portion of the outer blade 3, namely, a time interval that the solenoid valves 12a and 12b are opened to supply the compressed air from the pump 11, thereby moving forward the inner blade 4 to close the aspiration port 3a. An OPEN time T2 indicates a time interval to open the aspiration port 3a, namely, a time interval that the solenoid valves 12a and 12b are closed to stop the supply of the compressed air, thereby moving backward the inner blade 4 to open the aspiration port 3a. An OPEN ratio T2/ST shows the ratio of the OPEN time T2 to a one cycle time ST, namely, the ratio of the closing time of the solenoid valves 12a and 12b to the one cycle time ST.

When the set value of the cutting speed CV is in a range of 50 to 450 cpm, the CLOSE time T1 in one cycle time is determined to be 50 msec in order to ensure the amount of aspiration, and the OPEN time T2 is adjusted to be shorter so that the one cycle time ST is reduced.

It is also desirable to control the CLOSE time T1 at 50 msec even when the set value of the cutting speed CV is 500 cpm or more; however, the OPEN time T2 will become shorter. Therefore, the CLOSE time T1 is adjusted to be gradually shorter as a cutting speed set value is increased, thereby shortening the one cycle time ST. In this case, the OPEN ratio T2/ST is 60%, almost constant, for the cutting speed of 500–850 cpm. For a high-speed range of 900–1800 cpm, the OPEN ratio T2/ST is increased as the speed is raised. Thus, the ratio of reduction in the aspiration flow amount caused in association with the speedup of the cutter 1 can be prevented. In other words, the aspiration flow amount is ensured as much as possible during the high-speed operation of the cutter 1 as well to provide high aspiration pressure. This good aspiration with respect to the vitreous body V into the aspiration port 3a enables efficient excision of the vitreous body V.

Considering only the excision efficiency during the high-seed operation, the CLOSE time T1 may be controlled to be 10 msec corresponding to the cutting speed of 1800 cpm. However, a vitreous body cutter incapable of operating if the CLOSE time T1 is 10 msec can not be driven even if the cutting speed is adjusted to lower settings. Accordingly, the CLOSE time is controlled to become longer as the speed is decreased as shown in FIG. 5. For example, a vitreous body cutter operable at the CLOSE time T1 of 18 msec can carry out surgery at the speed of at least 1200 cpm.

It is to be noted that control of the vitreous body cutter may be performed by changing the ratio between the opening time and the closing time of the solenoid valves without changing the cutting speed. For example, in the surgery on the center portion of an eyeball, the ratio of the closing time to the opening time of the solenoid valves 12a and 12b is increased, thereby lengthening the open time of the aspiration port 3a to raise excision efficiency. In the surgery on the periphery of a retina, on the other hand, the ratio of the opening time to the closing time of the solenoid valves 12a and 12b is increase, thereby shortening the open time of the aspiration port 3a to suppress the behavior or the retina caused by intermittent aspiration.

As explained above, according to the present invention, a vitreous body cutter can be actuated at a high speed by a simple structure, thereby enabling smooth excision with respect to a vitreous body around the retina. Furthermore, the noise of the apparatus can be reduced, aspiration efficiency during high-speed actuation can be further enhanced with good cutting sharpness for surgery.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A vitreous surgical apparatus in which an inner tubular blade is moved in an axis direction with respect to an outer tubular blade by supply and exhaust of compressed air to excise a part of a vitreous body in an eyeball and aspirate and discharge the excised part out of the eyeball by an aspiration pressure applied by an aspiration pump, the apparatus comprising:

a first solenoid valve which is opened and closed for performing the supply and exhaust of the compressed air;

a second solenoid valve which is opened and closed for performing the supply and exhaust of the compressed air; and control means which drives each of the first and second solenoid valves to open synchronously and to close synchronously in order to move the inner tubular blade at a desired high cutting speed.

2. The vitreous surgical apparatus according to claim 1, wherein, when the cutting speed is set at a predetermined value or more, the control means increases a ratio of a closing time of the solenoid valves to an opening time in one cycle time.

3. The vitreous surgical apparatus according to claim 2, wherein the predetermined value of the cutting speed includes about 1000 cpm.

4. The vitreous surgical apparatus according to claim 1, wherein, as the cutting speed is set at a higher value, the control means gradually shortens an opening time of the solenoid valves in a cycle time and gradually lengthens a closing time of the solenoid valves in the cycle time.

5. The vitreous surgical apparatus according to claim 1, wherein the control means changes a ratio between an opening time and a closing time of the solenoid valves without changing a cutting speed.

6. A vitreous surgical apparatus for excising a part of a vitreous body in an eyeball and aspirating and discharging the excised part out of the eyeball by an aspiration pressure applied by an aspiration pump, the apparatus comprising:

an outer tubular blade;

an inner tubular blade movable in an axis direction with respect to the outer tubular blade;

a piston to which the inner tubular blade is fixed;

an air chamber in which the piston is movably disposed;

a first solenoid valve having a first output port being in communication with the air chamber, a first aspiration port being in communication with a compressed air supply source, and a first exhaust port through which the compressed air is exhausted, the first solenoid valve being switched between 1) communication between the first output port and the first aspiration port for opening the valve and 2) communication between the first output port and the first exhaust port for closing the valve to alternately perform supply and exhaust of the compressed air to and from the air chamber;

a second solenoid valve having a second output port being in communication with the air chamber, a second aspiration port being in communication with a compressed air supply source, and a second exhaust port through which the compressed air is exhaust, the second solenoid valve being switched between 1) communication between the second output port and the second aspiration port for opening the valve and 2) communication between the second output port and the second exhaust port for closing the valve to alternately perform supply and exhaust of the compressed air to and from the air chamber: and a control section which drives each of the first and second solenoid valves to open synchronously and to close synchronously in order to move the inner tubular blade at a desired high cutting speed.

7. The vitreous surgical apparatus according to claim 6 further comprising an air room which is in communication with each exhaust port.

8. The vitreous surgical apparatus according to claim 6, wherein, when the cutting speed is set at a predetermined value or more, the control section increases a ratio of a time that each output port is in communication with each exhaust port to a time that each output port is in communication with each aspiration port in a cycle time.

9. The vitreous surgical apparatus according to claim 8, wherein the predetermined value of the cutting speed includes about 1000 cpm.

10. The vitreous surgical apparatus according to claim 6, wherein, as the cutting speed is set at a higher value, the control section gradually shortens a time that each output port is in communication with each aspiration port in a cycle time and gradually lengthens a time that each output port is in communication with each exhaust port in the cycle time.

11. The vitreous surgical apparatus according to claim 6, wherein the control section changes a ratio between an opening time and a closing time of the solenoid valves without changing a cutting speed.

12. A vitreous surgical apparatus in which an inner tubular blade is moved in an axis direction with respect to an outer tubular blade by supply and exhaust of compressed air to excise a part of a vitreous body in an eyeball and aspirate and discharge the excised part out of the eyeball by an aspiration pressure applied by an aspiration pump, the apparatus comprising:

a first solenoid valve which is opened and closed for performing the supply and exhaust of the compressed air;

a second solenoid valve which is opened and closed for performing the supply and exhaust of the compressed air; and control means which drives each of the first and second solenoid valves, the control means being adapted to change a cutting speed from a low speed range to a high speed range, to determine a time (T1), which is for opening each solenoid valve to supply the compressed air, to be constant in the low speed range, and to increase a ratio (T2/ST) of a time (T2), which is for closing each solenoid valve to stop the supply of the compressed air, to one cycle time (ST) in the high speed range than a constant ratio (T2/ST) in a medium speed range in order to prevent a ratio of reduction in an aspiration flow amount in the high speed range.

* * * * *